United States Patent
Miura

(10) Patent No.: US 9,896,706 B2
(45) Date of Patent: Feb. 20, 2018

(54) METHOD FOR PRODUCING β-GLUCAN

(71) Applicant: Shigenobu Miura, Tokyo (JP)

(72) Inventor: Shigenobu Miura, Tokyo (JP)

(*) Notice: Subject to any disclaimer, the term of this patent is extended or adjusted under 35 U.S.C. 154(b) by 40 days.

(21) Appl. No.: 14/415,574

(22) PCT Filed: May 29, 2013

(86) PCT No.: PCT/JP2013/064862
§ 371 (c)(1),
(2) Date: Jan. 16, 2015

(87) PCT Pub. No.: WO2014/013793
PCT Pub. Date: Jan. 23, 2014

(65) Prior Publication Data
US 2015/0152454 A1    Jun. 4, 2015

(30) Foreign Application Priority Data
Jul. 17, 2012  (JP) ................ 2012-158805

(51) Int. Cl.
| C12P 39/00 | (2006.01) |
| C12P 19/04 | (2006.01) |
| A61K 31/716 | (2006.01) |
| C12R 1/645 | (2006.01) |
| C08B 37/00 | (2006.01) |

(52) U.S. Cl.
CPC .......... C12P 19/04 (2013.01); A61K 31/716 (2013.01); C08B 37/0024 (2013.01); C12R 1/645 (2013.01)

(58) Field of Classification Search
None
See application file for complete search history.

(56) References Cited

U.S. PATENT DOCUMENTS 5,019,514 A * 5/1991 Bock ............... C12P 19/10
435/254.11
2012/0202771 A1   8/2012 Moriya et al.

FOREIGN PATENT DOCUMENTS

| JP | 2005-220065 | * | 8/2005 |
| JP | 2005220065 A | | 8/2005 |
| JP | 2006075076 A | | 3/2006 |
| JP | 2009056391 A | | 3/2009 |
| JP | 2010094078 A | | 4/2010 |
| JP | 2011254789 A | | 12/2011 |
| WO | 2011043435 A1 | | 4/2011 |

OTHER PUBLICATIONS

Endres et al., Food and Chemical Toxicology 47: 1231-1238 (2009).*
Barata et al., Int. J. Food Microbiol. 153: 243-259 (2012).*
ISA Japanese Patent Office, International Search Report of PCT/JP2013/064862, dated Aug. 6, 2013, 4 pages.
Hirata, Makoto, "Development of Recycling Technology for Organic Waste", Oita University Venture Business Laboratory Annual Report, Available as early as Jan. 1, 2005, pp. 48-52.
Sanders, et al., "Sporeformers as Human Probiotics: Bacillus, Sporolactobacillus, and Brevibacillus", Comprehensive Reviews in Food Science and Food Safety, vol. 2, Jul. 2003, 10 pages.
Masuko, et al. "Carbohydrate analysis by a phenol-sulfuric acid method in microplate format." Analytical biochemistry vol. 339, No. 1, Apr. 1. 2005, pp. 69-72.
Endres, J.R. et al. "Safety assessment of a proprietary preparation of a novel Probiotic, Bacillus coagulans, as a food ingredient" Food and Chemical Toxicology, vol. 47, No. 6, Jun. 2009, pp. 1231-1238.
Miyawaki, Kaori et al., "Relationship between the functional B-glucan polysaccharide-production and the cell morphologies of Aureobasidium pullans", Seibutsu-Kogaku Kaishi, vol. 88, No. 12, Dec. 2010, pp. 634-641.

* cited by examiner

*Primary Examiner* — Erin M. Bowers
(74) *Attorney, Agent, or Firm* — Alleman Hall Creasman & Tuttle LLP

(57) ABSTRACT

It is an object of the present invention to provide a method for producing β-glucan having excellent immunopotentiating effects at a lower cost. Black yeast (*Aureobasidium pullulans*) is cultured using cells of lactic acid-producing bacteria and/or derivatives thereof as a nutrient source and is allowed to produce β-glucan.

7 Claims, No Drawings

METHOD FOR PRODUCING β-GLUCAN

TECHNICAL FIELD

The present invention relates to a method for producing β-glucan having excellent immunopotentiating effects.

BACKGROUND ART

Recently, β-glucan (β-1, 3-1, 6-glucan) attracts attention due to its immunopotentiating effects. That is, β-glucan serves to activate macrophages, NK cells, T cells, killer T cells and the like that attack infected cells and cancer cells in the body, and exhibits effects of eliminating bacteria and foreign matter that have entered the body and suppressing the onset of disease by increasing immunity and resistance. Also, it has been reported that as a result of exhibiting these effects, β-glucan has functions such as suppressing allergies, suppressing malignant tumors such as cancer, reducing blood sugar levels, promoting urination, adjusting blood pressure, and reducing blood cholesterol levels and neutral lipid levels.

As methods for producing β-glucan, a method for extracting β-glucan from baker's yeasts and mushrooms, and a method in which black yeast (*Aureobasidium pullulans*) is cultured to accumulate β-glucan in the culture medium, are used. It is considered that β-glucan derived from black yeast has higher water solubility than β-glucan derived from other organisms, and has the advantage of being highly effective due to its molecular structure in which the 1.6 chain is densely branched.

The immunopotentiating effects of lactic acid bacteria and of lactic acid-producing bacteria belonging to the genus *Bacillus* have already been known, and there are many reports thereupon. It is known that these bacteria producing lactic acid have relatively many specific base sequences (DNA fragments) called CpG motifs as components of their cell walls. It is conceivable that the CpG motifs directly stimulate the immune system of mammals to activate macrophages, NK cells, T cells, killer T cells and the like, and to enhance their defense systems against various types of infections.

It should be noted that the term "lactic acid bacteria" is not a bacterial name that is mycologically defined, and its definition is derived from the application of the family name Lactobacteriaceae to gram-positive bacilli and cocci that ferment sugar to produce only lactic acid or to produce lactic acid, acetic acid, alcohol, and carbonic acid gas.

Moreover, lactic acid-producing bacteria belonging to the genus *Bacillus* are sometimes called spore-forming lactic acid bacteria, but are not classified as common lactic acid bacteria.

Physiologically active effects of *Bacillus coagulans* have also been widely known, and its usefulness in probiotics has been found. Moreover, the safety of this bacterial strain is also as widely recognized as the safety of common lactic acid bacteria is (Non-Patent Documents 1 and 2).

A finished product in which β-glucan and lactic acid bacteria are mixed in a combination has been developed, and it is reported that in particular, a composition in which β-glucan and *Enterococcus faecalis,* which is a lactic acid coccus, are combined exhibits effects for enhancing immunity to influenza and preventing the exacerbation thereof (Patent Document 1).

CITATION LIST

Patent Documents

Patent Document 1: JP 2005-220065A

Non-Patent Documents

Non-Patent Document 1: Comprehensive Reviews in Food Science and Food Safety, 2(3), 101-110
Non-Patent Document 2: Food Chem Toxicol, 47(6), 1231-1238 (2009)

SUMMARY OF THE INVENTION

Technical Problems

In the conventional method for producing β-glucan using black yeast, it is necessary to use natural products such as rice bran, as well as sugar, as nutrient sources of a culture medium. However, rice bran and the like remain in the finished products as impurities and are difficult to separate therefrom in a later step. Presence of such impurities affects the texture and quality of taste of food.

Moreover, β-glucan is not toxic, but the ingestion of a large amount of β-glucan sometimes causes a symptom of diarrhea. Therefore, it is thought that the ingestion of a combination of lactic acid bacteria or the like and β-glucan that differ in the action mechanisms of immunopotentiation is preferable in order to obtain sufficient immunopotentiating effects.

Generally, cells of lactic acid bacteria that are used as lactic acid bacteria to be mixed with β-glucan are obtained by culturing lactic acid bacteria in a culture medium in which inorganic salts, vitamins, a nutrient source such as yeast extract, and the like are added to a sugar source such as glucose, then sterilizing this culture medium at a high temperature and under a high pressure, then separating the bacterial cells from the culture medium by microfiltration, centrifugation, or the like. This finished product is in the form of a powder that is diluted by powdery dextrin or the like, for example, and is very expensive.

Moreover, it is known that large quantities of common lactic acid bacteria belonging to the genera *Lactobacillus, Lactococcus,* and the like, and lactic acid-producing bacteria belonging to the genus *Bacillus,* such as the genus *Sporolactobacillus,* grow by lactic acid fermentation when lactic acid is industrially produced. These bacteria producing lactic acid are separated from the culture medium with a flocculant, a filter aid, or the like after the lactic acid fermentation is finished, and most of them are discarded as they are.

Accordingly, the present invention was made in order to provide a method for producing β-glucan having excellent immunopotentiating effects at a lower cost.

Solution to Problem

The inventor of the present invention thought that if lactic acid-producing bacteria (including common lactic acid bacteria and lactic acid-producing bacteria belonging to the genus *Bacillus*), which are waste products of lactic acid fermentation, could be used as a nutrient source of β-glucan cultures, it would be possible to inexpensively create a finished product that exhibited effects of both β-glucan and lactic acid-producing bacteria. Then, the inventor of the present invention found that it was possible to efficiently produce a culture solution containing β-glucan with less impurities by culturing black yeast, which are β-glucan-producing bacteria that can grow using waste lactic-acid producing bacteria after lactic acid fermentation is finished as the only nitrogen source, under appropriate conditions. The present invention was accomplished based on these findings.

That is, a method for producing β-glucan according to the present invention includes a step of allowing black yeast (*Aureobasidium pullulans*) to produce β-glucan by culturing the black yeast using cells of lactic acid-producing bacteria and/or derivatives thereof as a nutrient source. It should be noted that in the present invention, the term "lactic acid-producing bacteria" is used as a general term for bacteria that can produce lactic acid, and is used in a broad sense and refers not only to lactic acid-producing bacteria belonging to the genus *Bacillus* but to both common lactic acid bacteria and lactic acid-producing bacteria belonging to the genus *Bacillus*.

It is preferable that the black yeast can grow using cells of a lactic acid-producing bacteria and/or derivatives thereof as an only nitrogen source.

In particular, among such black yeasts, *Aureobasidium pullulans* MRB001(Accession number: NITE BP-1386) is preferably used. This strain was deposited in the Patent Microorganisms Depositary of the National Institute of Technology and Evaluation (NPMD) (2-5-8, Kazusakama-tari, Kisarazu-shi, Chiba, Japan) on Jul. 5, 2012, and is publicly available.

*Bacillus coagulans* can be used as the lactic acid-producing bacteria. It should be noted that no known documents disclose a case where *Bacillus coagulans* and β-glucan are used in a combination to enhance immunopotentiating effects or the like.

A composition containing β-glucan that contains β-glucan obtained by the production method according to the present invention is also one of the present inventions. β-Glucan obtained by the production method according to the present invention exhibits superior immunopotentiating effects to β-glucan obtained by a conventional method. It is thought that this is because DNA fractions, including the CpG motifs that are included in the cell walls of lactic acid-producing bacteria, are mixed into the β-glucan obtained by the production method according to the present invention.

Furthermore, the black yeast, *Aureobasidium pullulans* MRB001 (Accession number: NITE BP-1386), is also one of the present inventions.

Advantageous Effects of the Invention

With the present invention having such a configuration, it is possible to use, as a raw material, lactic acid-producing bacteria that include many CpG motifs as components of their cell walls and exhibit immunopotentiating effects, to produce a large amount of β-glucan that exhibits similar immunopotentiating effects at a low cost without using other nitrogen sources, such as rice bran, that remain as impurities. Accordingly, with the present invention, a finished product having a high purity that can synergistically exhibit the immunopotentiating effects of lactic acid-producing bacteria and β-glucan can be obtained.

Also, the present invention can be utilized as a useful method for using lactic acid-producing bacteria that are discarded in large quantities after lactic acid fermentation for producing monomers of polylactic acid that have recently attracted attention as bioplastics and are anticipated to be produced in large amounts. Therefore, it is possible to expand the utilization range of β-glucan and lactic acid-producing bacteria from its current use in parts of health foods and pet foods to use in livestock feed and the like at a low cost. Also, the present invention is useful for preventing avian influenza and the like, and the impact on the economy is expected to be considerable.

DESCRIPTION OF EMBODIMENTS

Hereinafter, the present invention will be described in detail.

The method for producing β-glucan according to the present invention includes a step of allowing black yeast (*Aureobasidium pullulans*) to produce β-glucan by culturing the black yeast using cells of lactic acid-producing bacteria and/or derivatives thereof as a nutrient source.

There is no particular limitation on the lactic acid-producing bacteria as long as the bacteria can produce lactic acid, and, for example, common lactic acid bacteria, lactic-acid producing bacteria belonging to the genus *Bacillus* (also referred to as "*Bacillus* lactic acid-producing bacteria" hereinafter), and the like are used. It is known that these lactic acid-producing bacteria include many specific base sequences called CpG motifs in the DNA of their cell walls.

Common lactic acid bacteria accumulate lactic acid in a culture medium in conjunction with their proliferation. Lactic acid bacteria include homo lactic acid bacteria, which produce only lactic acid as a final product, and hetero lactic acid bacteria, which simultaneously produce substances other than lactic acid, such as alcohol and acetic acid. Homo lactic acid bacteria are used for a common production of lactic acid. Moreover, lactic acid bacteria are classified as lactic acid cocci or lactic acid bacilli based on their shapes. It is supposed that lactic acid cocci are often used industrially.

Typical examples of lactic acid bacteria include six genera, which are *Lactobacillus, Bifidobacterium, Enterococcus, Lactococcus, Pediococcus,* and *Leuconostoc*. All of these are gram-positive bacteria, and produce a large amount of lactic acid by fermentation. Many strains of lactic acid bacteria produce L-lactic acid. Some strains belonging to the genus *Lactobacillus* produce D-lactic acid, and other strains produce L-lactic acid and D-lactic acid in certain ratios.

Examples of *Bacillus* lactic acid-producing bacteria that mainly produce D-lactic acid include *Bacillus laebolacticus* and bacteria belonging to the genus *Sporolactobacillus*. These bacteria can be treated in the same manner as common lactic acid bacteria, and used to produce D-lactic acid.

Examples of *Bacillus* lactic acid-producing bacteria that mainly produce L-lactic acid include *Bacillus coagulans*.

Considering the efficiency of lactic acid fermentation, among these lactic acid-producing bacteria, examples of strains that are generally used in lactic acid fermentation and are readily available include lactic acid bacteria that produce L-lactic acid and belong to the genera *Lactobacillus, Lactococcus,* and the like, *Bacillus* lactic acid-producing bacteria that produce D-lactic acid such as *Bacillus laebolacticus,* and bacteria belonging to the genus *Sporolactobacillus,* and *Bacillus coagulans* that produce L-lactic acid. Among these, the strains of *Bacillus coagulans* can perform lactic acid fermentation at a high temperature, and therefore the possibility of contamination is reduced and it is easier to separate the bacterial cells from the culture medium for lactic acid fermentation as compared with common lactic acid bacteria. Moreover, it was confirmed that when *Bacillus coagulans* is used as a nutrient source, the productivity of β-glucan by black yeast is high.

Lactic acid fermentation is generally performed as follows. That is, in order to perform lactic acid fermentation using common lactic acid bacteria, a culture medium is prepared that is obtained by adding a small amount of nutrient component serving as a nitrogen source, such as yeast extract, peptone, soybean hydrolysate, corn steep liquor and/or others, to a main component serving as a carbon source, such as starch, liquefied starch, saccharified starch, raw sugar, and/or glucose, and by adding inorganic salts such as potassium dihydrogenphosphate and magnesium sulfate, and vitamins thereto if needed, then a seed culture solution of lactic acid bacteria is added thereto, and fermentation is performed at a temperature suitable for lactic acid bacteria for use under an anaerobic condition while the pH during fermentation is adjusted to an appropriate value using a neutralizer such as calcium hydroxide, calcium carbonate and/or sodium hydroxide.

On the other hand, in order to perform fermentation using *Bacillus* lactic acid-producing bacteria such as *Bacillus coagulans*, the bacteria are cultured under an aerobic condition in a culture medium that contains sugar such as starch, liquefied starch, saccharified starch, raw sugar, and/or glucose as a main component at a relatively low concentration, to which a small amount of nutrient components such as yeast extract, peptone, soybean hydrolysate, corn steep liquor and others are added, and inorganic salts such as potassium dihydrogenphosphate and magnesium sulfate, and vitamins are added if needed. Then, the carbon source is additionally introduced thereinto as a main component, the culture medium is placed in an anaerobic condition and is maintained at an appropriate temperature, and fermentation is performed while the pH during fermentation is adjusted to an appropriate value using a neutralizer such as calcium hydroxide, calcium carbonate and/or sodium hydroxide. Such fermentation allows the bacteria to produce lactic acid in the culture medium. Also, lactic acid fermentation may be similarly performed after separating bacterial cells and a culture medium at the time when aerobic culture is finished, then adding the bacterial cells to a culture medium obtained by adding a small amount of another nutrient component to a culture medium containing a carbon source at a high concentration, and maintaining the culture medium in an anaerobic condition. During culture of *Bacillus coagulans*, an appropriate temperature is generally equal to or greater than 50° C., and equal to or greater than 55° C. for some strains. Therefore, since the culture medium is unlikely to be contaminated, such culture is particularly preferable when bacterial cells are the objective.

It is easy to obtain wet bacterial cells from the culture medium after the fermentation by separation using a desk-type centrifugal separator or filtration using a filter with a pore size of 1 µm or less, such as pressure filtration, vacuum filtration and cross flow filtration. The yield of the wet bacterial cells is generally several grams to several tens of grams per liter of a culture medium.

The black yeast is a strain of *Aureobasidium pullulans*. The black yeast is a type of mold that can be easily isolated from the soil, the surface of a plant, or the like. The black yeast generally produces pullulan, and it is known that it produces water-soluble β-glucan (β-1, 3-1, 6-glucan) outside of its cells under some culture conditions (see Seibutsu-kogaku Kaishi, 88(12), 634-641, 2010).

There is no particular limitation on the strain of the black yeast used, and the strain may be selected from known strains and used as appropriate, or a strain that has been subjected to mutagenesis treatment so as to produce substantially no melanin pigments, as described in JP 2006-75076A and JP 2009-56391A, may be used. In particular, black yeast that can grow using the cells of lactic acid-producing bacteria and/or derivatives thereof as an only nitrogen source is preferable as the black yeast, and furthermore, a mutant strain mutated so as to have high productivity when growing using the cells of lactic acid-producing bacteria and/or derivatives thereof as the only nitrogen source is even more preferable. The use of such a mutant strain allows a large amount of β-glucan to be efficiently produced at a low cost.

Such a mutant strain can be obtained by subjecting black yeast as a mother strain to common mutagenesis treatment, allowing the black yeast to grow using the cells of lactic acid-producing bacteria and/or derivatives thereof as the only nitrogen source, and then selecting strains that grow better.

More specifically, it is possible to perform a screening of superior strains of black yeast as follows. That is, mother strains of *Aureobasidium pullulans* that produce β-glucan are subjected to mutagenesis treatment on agar culture media that contain a carbon source such as sucrose, wet cells of lactic acid-producing bacteria as a nitrogen source, ascorbic acid or a sodium salt thereof for adjusting the pH, and the like. Strains that grow better are selected, are inoculated into a liquid culture medium containing lactic acid-producing bacteria as the only nitrogen source and are shake-cultured. Then, strains having a high β-glucan-producing ability are selected.

There is no particular limitation on the mutagenesis treatment, and examples thereof include ultraviolet ray irradiating treatment and mutagenizing drug treatment.

There is no particular limitation on the mutagenizing drugs, and, for example, it is possible to use common mutagenizing agents such as nitrosoguanidine, ethidium bromide, ethyl methanesulfonate, and sodium nitrite.

There is no particular limitation on the mother strains subjected to mutagenesis treatment as long as they are the strains of *Aureobasidium pullulans*, and strains that are newly isolated from nature or stock strains that are conventionally known to produce β-glucan may be used. Examples of such stock strains include *Aureobasidium pullulans* ATCC 9348, ATCC 3092, ATCC 42023, IFO 4464, IFO 4466, IFO 6353, and IFO 7757.

After the mutagenesis treatment, colonies on agar culture media are selected based on their size. It is preferable that the strains selected based on their colony size are further shake-cultured in flasks containing a liquid culture medium that contains lactic acid-producing bacteria as the only nitrogen source, the production of β-glucan is checked, and strains that have higher productivity than that of the mother strains are selected.

The inventor of the present invention succeeded in obtaining *Aureobasidium pullulans* MRB001 (Accession number: NITE BP-1386) using such a screening method.

When inoculated into a sterilized liquid medium containing sucrose, rice bran, sodium ascorbate, and the like, shake-cultured at 20 to 30° C. for several days, and stored in a sterilely divided and frozen state, the selected mutant strains can be used as an inoculum with high reproducibility.

In order to culture black yeast using lactic acid-producing bacteria as a nitrogen source to allow the black yeast to produce β-glucan, the following method can be used, for example. That is, black yeast is inoculated into a liquid culture medium obtained by adding an appropriate amount of lactic acid-producing bacteria as a nitrogen source and a small amount of ascorbic acid to a carbon source such as sucrose, and then shake-cultured using a flask, for example.

It is sufficient to set the concentration of each component as appropriate considering the properties of culture solution to be made into a finished product, and generally, for example, the concentration of sucrose is about 10 to 20 g/L and the concentration of ascorbic acid is about 1 to 3 g/L.

There is no particular limitation on a form of lactic acid-producing bacteria to be added to the liquid culture medium, and examples thereof may include the culture obtained by culturing a strain of lactic acid-producing bacteria in an appropriate culture medium, bacterial cells separated from the culture, homogenate of the bacterial cells, lysate of the bacterial cells, extract of the bacterial cells, and fractions thereof. Moreover, the lactic acid-producing bacteria may be used in a form of dead bacterial cells or viable bacterial cells, and wet bacterial cells or dry bacterial cells.

Since the appropriate additional quantity of lactic acid-producing bacteria varies depending on the bacterial strain and form, it is preferable to determine the optimum quantity in advance by performing experiments. If the additional quantity of lactic acid-producing bacteria is small, a nitrogen source runs short, and even if it is too large, the amount of β-glucan produced is reduced.

Furthermore, if needed, a small amount of nutrient component such as rice bran may be added as long as there is no influence on the quality of taste, the specifications of a finished product, and the like. When rice bran is supplementarily added in this manner, it is added in an amount of about 1 to 4 g/L. However, when a mutant strain is used as the black yeast for culture, the addition of rice bran is unnecessary.

The pH of the liquid culture medium generally becomes 4.5 to 6 without particularly adjusting the pH as long as the liquid culture medium has the above-described composition, and the liquid culture medium can be used for the culture of black yeast as it is. It is preferable to further adjust the pH using ascorbic acid or the like to a pH that is preferable for the culture of black yeast. It should be noted that the pH that is preferable for the culture of black yeast is 5 to 6. The culture temperature is generally 20 to 30° C., and preferably 24 to 25° C.

When the culture is performed using a jar fermenter, the composition of a culture medium and the culture temperature are set to be the same as those in the case where a flask is used, and the aeration rate and rotation rate are adjusted so as to maintain DO at a concentration that is 15% or more, and preferably 20% or more, of the saturated concentration before the inoculation. The viscosity of the culture solution gradually increases after the start of the culture, the remaining sugar is generally used up in 4 to 6 days, and thus the culture is finished. It is possible to determine the end of the culture based on the increase of DO. β-glucan is produced in an amount of about 2 to 4 g/L when shake-culturing using a flask is performed, and 6 g/L or more when a jar fermenter is used.

In order to industrially produce a large amount of β-glucan, it is sufficient to use a culture apparatus capable of ventilating and stirring a culture medium to some extent. As such a culture apparatus, for example, a common stirring-type fermenter, an air lift-type fermenter, or the like is used. It is sufficient to adjust the aeration rate as appropriate depending on the size and the type of a fermenter. In particular, an air lift-type fermenter with low power-consumption is preferable considering an economical benefit because such equipment is relatively inexpensive.

It was revealed that the ratio of conversion from a raw material (sucrose) to β-glucan is comparatively higher in the culture solution of black yeast that is produced as described above and contains β-glucan compared with the culture solution of black yeast cultured in a conventional rice bran culture medium, or the like. Furthermore, the components of the culture medium, such as rice bran, do not affect the quality of taste. Since the components derived from lactic acid bacteria (particularly the components derived from the cell wall) are contained, it is anticipated that immunopotentiating effects are also high.

Concerning a synergistic effect due to the components derived from lactic acid bacteria, it is supposed that DNA fragments including the CpG motifs contained in the cell walls of lactic acid-producing bacteria are effectively incorporated in the side chains or the like of β-glucan produced by black yeast, and adsorb together with the β-glucan on the surfaces of cells of mammals that ingested the β-glucan, and thus their immune systems are effectively stimulated.

The culture solution of black yeast using lactic acid-producing bacteria as a nitrogen source, which is produced in this manner, can be made into a finished product as a composition containing β-glucan as it is after being sterilized by any method. Also, lactic acid-producing bacteria separated from a culture medium for lactic acid fermentation may be further added to the culture solution of black yeast regardless of whether they are dead bacterial cells or viable bacterial cells, and the mixture may be made into a finished product. A finished product may be in liquid form as the culture solution is, but it is preferable to process the culture solution so as to be easy to ingest. For example, the culture medium may be made into powder by a spray drying method or the like, or may be mixed into other solid materials or liquid materials.

EXAMPLES

Hereinafter, the present invention will be described more specifically by way of examples, but the present invention is not limited to the following examples.

In the following, lactic acid in a culture medium was measured using a high speed liquid chromatography. β-glucan was quantified with reference to a method described in JP 2006-75076A. Furthermore, β-glucan was also quantified using a phenol-sulfuric acid method (Analytical Biochemistry, 339(1), 69-72 (2005)) as a simple quantification method. In the following, defatted rice bran obtained in Thailand was used as the rice bran.

Experimental Example 1

Culture of Lactic Acid-Producing Bacteria (*Bacillus Coagulans*)

*Bacillus coagulans* IFO12714, which are *Bacillus* lactic acid-producing bacteria, were inoculated into a 5000 mL jar fermenter containing 1000 mL of a culture medium having a composition shown in Table 1, and were aerobically cultured with an aeration rate of 1.0 vvm at a stirring rotation rate of 400 rpm at 50° C. for 8 hours.

TABLE 1

| | |
|---|---|
| Glucose | 30 g |
| Yeast extract | 12 g |
| Polypeptone | 12 g |
| Monopotassium phosphate | 0.6 g |
| Magnesium sulfate | 0.3 g |
| pH | 6.1 |

*The volume of the above culture medium was adjusted to 1000 mL by adding water. The culture medium was then sterilized at 120° C. for 15 minutes. Ten grams of calcium carbonate that had been separately sterilized were added, and then the culture medium was used for culture.

Next, 2000 mL of a culture medium having a composition shown in Table 2 was added to the jar fermenter, and lactic acid fermentation was advanced by anaerobically culturing the bacteria at a stirring rotation rate of 50 rpm for 25 hours.

TABLE 2

| | |
|---|---|
| Glucose | 330 g |
| Yeast extract | 3 g |
| Polypeptone | 3 g |

*The volume of the above culture medium was adjusted to 2000 mL by adding water. The culture medium was then sterilized at 120° C. for 15 minutes. Three hundred grams of calcium carbonate that had been separately sterilized were added, and then the culture medium was used for culture.

The concentration of lactic acid was 108 g/L when the fermentation was finished. This culture medium was subjected to high-speed centrifugation (6000 G, 10 minutes), and 80.1 g of precipitated wet cells of *Bacillus* were obtained (the weight of dry bacterial cells was about 20%).

Experimental Example 2

Separation and Culture of Black Yeast

Samples of microorganisms collected from the soil, food factories, starch factories, surfaces of plants, and the like were applied to potato dextrose agar culture media, and colonies of microorganisms having properties that were similar to those of black yeast (viscous white or pinkish colonies, which turn brown/black when allowed to stand) were visually selected and separated from a lot of obtained colonies of microorganisms.

Next, these microbial cells were inoculated into liquid culture media (rice bran culture media) having a composition shown in Table 3 and cultured at 24° C. for 5 days. Strains whose culture media had high viscosity and were considered to obviously produce viscous polysaccharides were selected from those microbes, and β-glucan was quantified by analyzing precipitates obtained by adding ethanol in an amount equal to that of the culture medium by the simple quantification method. The strain that produced the largest amount of β-glucan among those microbes accumulated β-glucan at a concentration of 5.2 g/L in the culture medium. This strain was used in the following experiments.

TABLE 3

| | |
|---|---|
| Sucrose | 10 g |
| Rice bran | 2 g |
| Sodium ascorbate | 2 g |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

Next, the obtained microbial cells were suspended in PBS (phosphate buffered saline) so as to provide a solution of about 1000 CFU/mL with reference to the method described in JP 2005-75076A. Then, 0.2 mL of the solution was applied to an agar culture medium plate, ultraviolet ray irradiating treatment using an ultraviolet lamp was performed (the irradiation time was 2 to 10 minutes), and then the cells were cultured on the agar plate as they were at 24° C. for 4 days. Microbes that formed obvious colonies on the plate were cultured at 4° C. for another three days, and were allowed to form chlamydospores. Colonies having a white appearance were selected from such colonies, and a mutant strain that produced no melanin pigments was obtained.

This microorganism was identified and determined as *Aureobasidium pullulans*, and was named *Aureobasidium pullulans* MR01.

*Aureobasidium pullulans* MR01 was inoculated into a 300 mL Erlenmeyer flask containing 100 mL of a culture medium shown in Table 3, and was shake-cultured at a stirring rotation rate of 150 rpm at 25° C. for 3 days. This was used as a seed for the following experiments.

Experimental Example 3

Obtainment of a mutant strain of black yeast

*Aureobasidium pullulans* MR01 cells obtained in Experimental Example 2 were suspended in PBS (phosphate buffered saline) so as to provide a solution of about 1000 CFU/mL. Then, 0.2 ml of the solution was applied to an agar culture medium plate having a composition shown in Table 4, and ultraviolet ray irradiating treatment using an ultraviolet lamp was performed. The irradiation time was 2 to 5 minutes. The cells were cultured on the agar plate as they were at 24° C. for 6 days, and then it was observed that white colonies that were smaller than colonies on a rice bran culture medium were formed. The hundred largest colonies were selected from such colonies in order of size.

TABLE 4

| | |
|---|---|
| Sucrose | 10 g |
| Sodium ascorbate | 2 g |
| Wet cells of *Bacillus* | 5 g (obtained in Experimental Example 1) |
| Agar | 15 g |

*The pH of the above culture medium was adjusted to 5.5 with ascorbic acid. The volume of the culture medium was adjusted to 1000 mL by adding water. The culture medium was sterilized at 120° C. for 15 minutes, and then agar plates were made.

Next, microbes were separated from the respective colonies, were inoculated into 300 mL Erlenmeyer flasks containing 100 mL of a culture medium having a composition shown in Table 5, and were shake-cultured at 24° C. for 4 days. The amount of β-glucan accumulated was analyzed by a simple quantification method. Table 6 shows the results.

TABLE 5

| | |
|---|---|
| Sucrose | 10 g |
| Sodium ascorbate | 2 g |
| Wet cells of *Bacillus* | 1 g |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

TABLE 6

| Amount of β-glucan accumulated (g/L) | Number of samples |
| --- | --- |
| 0-1.0 | 50 |
| 1.0-2.0 | 39 |
| 2.0-3.0 | 8 |
| 3.0-4.0 | 3 |

Maximum value: 3.4 g/L (Mother strain: 0.5 g/L)

The strain that produced the largest amount of β-glucan among these strains was named MRB001, and was cultured in a 300 mL Erlenmeyer flask containing 100 mL of a culture medium having a composition shown in Table 7 at 24° C. for 3 days. The culture solution was divided and stored at −80° C. in a frozen state.

TABLE 7

| Sucrose | 10 g |
| --- | --- |
| Rice bran | 2 g |
| Sodium ascorbate | 2 g |
| Wet cells of lactic acid-producing bacteria | 1 g |

*Lactobacillus rhamnosus* IFO3425 or *Bacillus coagulans* IFO12714 was used as the lactic acid-producing bacteria.
*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

The strain MRB001 was shake-cultured in a culture medium having a composition shown in Table 8 at 24° C. for 4 days. The amount of β-glucan produced was analyzed by a simple quantification method, and the optimum additional amount of wet bacterial cells was determined. Table 9 shows the results.

TABLE 8

| Sucrose | 10 g |
| --- | --- |
| Sodium ascorbate | 2 g |
| Wet cells of *Bacillus* | x g (x = 0, 0.5, 1, 2, 3, 5) |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

TABLE 9

| x (g) | Amount of β-glucan produced (g/L) |
| --- | --- |
| 0 | 0 |
| 0.5 | 1.4 |
| 1.0 | 3.0 |
| 2.0 | 4.6 |
| 3.0 | 4.0 |
| 5.0 | 3.6 |

It becomes clear from the results shown in Table 9 that the additional amount of lactic acid-producing bacteria (wet cells of *Bacillus* lactic acid-producing bacteria) has the optimum value.

Experimental Example 4

One hundred milliliters of a culture medium having a composition shown in Table 10 was fed to a 300 mL Erlenmeyer flask. The strain MRB001 was inoculated thereinto, and was shake-cultured at a stirring rotation rate of 150 rpm for 3 days as preculture.

TABLE 10

| Sucrose | 10 g |
| --- | --- |
| Wet cells of *Bacillus* | 2 g |
| Sodium ascorbate | 2 g |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

Next, 2700 mL of a culture medium having a composition shown in Table 11 was fed to a 5 L jar fermenter. Three hundred milliliters of the above-described preculture was added thereto, and culture was started with an aeration rate of 1 vvm at a stirring rotation rate of 400 rpm at 24° C.

TABLE 11

| Sucrose | 60 g |
| --- | --- |
| Wet cells of *Bacillus* | 6 g |
| Sodium ascorbate | 6 g |
| pH | 5.8 |

*The volume of the above culture medium was adjusted to 2700 mL by adding water. The culture medium was sterilized at 120° C. for 15 minutes, and then was used for culture.

Table 12 shows changes over time in the culture. The concentration of β-glucan was measured by the method for quantifying β-glucan described in JP 2006-75076A.

TABLE 12

| Time (h) | β-glucan concentration (g/L) | Note |
| --- | --- | --- |
| 0 | — | |
| 24 | 2.4 | |
| 48 | 3.2 | |
| 72 | 4.8 | Aeration rate changed to 1.5 vvm |
| 96 | 7.0 | |
| 120 | 7.9 | |
| 144 | 8.8 | |

It became clear from the results shown in Table 12 that it was possible to allow black yeast to produce β-glucan after lactic acid fermentation using dead cells (wet cells) of *Bacillus coagulans,* which are *Bacillus* lactic acid-producing bacteria, as the only nitrogen source.

Experimental Example 5

One hundred milliliters of a culture medium having a composition shown in Table 13 was fed to a 300 mL Erlenmeyer flask. The strain MRB001 was inoculated thereinto, and was shake-cultured at a stirring rotation rate of 150 rpm for 3 days as preculture.

TABLE 13

| Sucrose | 12 g |
| --- | --- |
| Wet cells of *Bacillus* | 2 g |
| Sodium ascorbate | 1 g |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

Next, 3000 mL of a culture medium having a composition shown in Table 14 was fed to a 5 L jar fermenter. Three hundred milliliters of the above-described preculture was added thereto, and culture was started with an aeration rate of 1 vvm at a stirring rotation rate of 400 rpm at 24° C.

TABLE 14

| | |
|---|---|
| Sucrose | 36 g |
| Wet cells of *Bacillus* | 6 g |
| Sodium ascorbate | 3 g |
| pH | 5.5 |

*The volume of the above culture medium was adjusted to 3000 mL by adding water. The culture medium was sterilized at 120° C. for 15 minutes, and then was used for culture.

The concentration of β-glucan was 8.8 g/L on the sixth day after the start of the culture. The concentration of β-glucan was measured by the method for quantifying β-glucan described in JP 2006-75076A. At that time, the concentration of remaining sugar that was measured by a phenol-sulfuric acid method was 2.0 g/L.

Experimental Example 6

One hundred milliliters of a culture medium having a composition shown in Table 15 was fed to a 300 mL Erlenmeyer flask. The strain MRB001 was inoculated thereinto, and was shake-cultured at a stirring rotation rate of 150 rpm for 3 days as preculture.

TABLE 15

| | |
|---|---|
| Sucrose | 12 g |
| Rice bran | 2 g |
| Sodium ascorbate | 1 g |

*The pH of the above culture medium was adjusted to 5.5 with ascorbic acid. The volume of the culture medium was adjusted to 1000 mL by adding water. The culture medium was sterilized at 120° C. for 15 minutes, and then was used for culture.

Next, 3000 mL of a culture medium having a composition shown in Table 16 was fed to a 5 L jar fermenter. Three hundred milliliters of the above-described preculture was added thereto, and culture was started with an aeration rate of 1 vvm at a stirring rotation rate of 400 rpm at 24° C.

TABLE 16

| | |
|---|---|
| Sucrose | 36 g |
| Rice bran | 6 g |
| Sodium ascorbate | 3 g |
| pH | 5.5 |

*The volume of the above culture medium was adjusted to 3000 mL by adding water. The culture medium was sterilized at 120° C. for 15 minutes, and then was used for culture.

The concentration of β-glucan was 7.4 g/L on the fifth day after the start of the culture. The concentration of β-glucan was measured by the method for quantifying β-glucan described in JP 2006-75076A. At that time, the concentration of remaining sugar that was measured by a phenol-sulfuric acid method was 1.8 g/L.

It became clear from the results of Experimental Examples 5 and 6 that it was possible to produce β-glucan with a higher selectivity in a culture medium using wet cells of *Bacillus* as a nitrogen source than in a culture medium using rice bran.

INDUSTRIAL APPLICABILITY

With the present invention, it is possible to produce β-glucan having excellent immunopotentiating effects at a lower cost.

The invention claimed is:

1. A method for producing β-glucan, the method comprising:
   (1) supplying living cells of *Aureobasidium pullulans* MRB001 with cells of a lactic acid-producing bacterium; and
   (2) culturing the living cells of *Aureobasidium pullulans* MRB001 in a medium in which the only nitrogen source present is the cells of the lactic acid-producing bacterium.

2. The method for producing β-glucan according to claim 1, wherein the lactic acid-producing bacterium is *Bacillus coagulans*.

3. The method for producing β-glucan according to claim 1, further comprising performing the following steps prior to step (1):
   (1-a) culturing the lactic acid-producing bacterium under aerobic conditions in a culture medium;
   (1-b) after culturing the lactic acid-producing bacterium under aerobic conditions, culturing the lactic acid-producing bacterium under anaerobic conditions in a culture medium; and
   (1-c) centrifuging or filtering the culture medium after culturing the lactic acid-producing bacterium under anaerobic conditions to obtain the cells of the lactic acid-producing bacterium cultured under anaerobic conditions.

4. The method for producing β-glucan according to claim 3, wherein step (1-c) further comprises centrifuging the culture medium at a gravitational acceleration of 6000×g for 10 minutes.

5. The method for producing β-glucan according to claim 1, wherein an amount of the cells of the lactic acid-producing bacterium present in the culture medium of step (2) is at least 0.5 g per 1 L of culture medium.

6. The method for producing β-glucan according to claim 1, wherein the living cells of *Aureobasidium pullulans* MRB001 are cultured for 4 to 6 days.

7. The method for producing β-glucan according to claim 1, wherein the living cells of *Aureobasidium pullulans* MRB001 are produced by a method comprising:
   collecting *Aureobasidium pullulans* from soil, food factories, starch factories, and/or surfaces of plants;
   subjecting the collected *Aureobasidium pullulans* to a first round of ultraviolet ray irradiating treatment or mutagenizing drug treatment;
   selecting strains of the collected *Aureobasidium pullulans* subjected to the first round of ultraviolet ray irradiating treatment or mutagenizing drug treatment that produce substantially no melanin pigments following the first round of ultraviolet ray irradiating treatment or mutagenizing drug treatment;
   subjecting the selected strains of *Aureobasidium pullulans* that produce substantially no melanin pigments to a second round of ultraviolet ray irradiating treatment or mutagenizing drug treatment; and selecting strains of *Aureobasidium pullulans* subjected to the second round of ultraviolet ray irradiating treatment or mutagenizing drug treatment that can utilize cells of the lactic acid-producing bacterium as a nutrient source following the second round of ultraviolet ray irradiating treatment or mutagenizing drug treatment to provide the living cells of *Aureobasidium pullulans* MRB001.

* * * * *